(12) United States Patent
Chen et al.

(10) Patent No.: US 10,821,071 B2
(45) Date of Patent: *Nov. 3, 2020

(54) TRANSDERMAL COMPOSITIONS OF IBUPROFEN AND METHODS OF USE THEREOF

(71) Applicant: Aponia Laboratories, Inc., Greenwich, CT (US)

(72) Inventors: Haigang Chen, Edina, MN (US); Gareth Winckle, Provence-Alps-Cote d'Azur (FR); Christopher Riley, Maryville, MO (US)

(73) Assignee: APONIA LABORATORIES, INC., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/808,220

(22) Filed: Nov. 9, 2017

(65) Prior Publication Data

US 2018/0125779 A1 May 10, 2018

Related U.S. Application Data

(63) Continuation of application No. 14/961,172, filed on Dec. 7, 2015, now Pat. No. 9,849,080, which is a (Continued)

(51) Int. Cl.
| | |
|---|---|
| *A61K 9/00* | (2006.01) |
| *A61K 47/12* | (2006.01) |
| *A61K 47/22* | (2006.01) |
| *A61K 47/20* | (2006.01) |
| *A61K 31/192* | (2006.01) |
| *A61K 47/18* | (2017.01) |

(Continued)

(52) U.S. Cl.
CPC .............. *A61K 9/0014* (2013.01); *A61K 9/06* (2013.01); *A61K 31/192* (2013.01); *A61K 47/10* (2013.01); *A61K 47/12* (2013.01); *A61K 47/14* (2013.01); *A61K 47/18* (2013.01); *A61K 47/20* (2013.01); *A61K 47/22* (2013.01); *A61K 47/38* (2013.01); *A61P 29/00* (2018.01)

(58) Field of Classification Search
None
See application file for complete search history.

(56) References Cited

U.S. PATENT DOCUMENTS

| 4,185,100 A | 1/1980 | Rovee et al. |
| 4,533,546 A | 8/1985 | Kishi et al. |

(Continued)

FOREIGN PATENT DOCUMENTS

| CA | 2294800 | 2/1999 |
| EP | 0151953 | 8/1985 |

(Continued)

OTHER PUBLICATIONS

Boots Pharmaceuticals, Ibuprofen Gel Information for the User (Apr. 2012).

(Continued)

*Primary Examiner* — Kyung S Chang
(74) *Attorney, Agent, or Firm* — Fish & Richardson P.C.

(57) ABSTRACT

A transdermal composition comprising ibuprofen or salts thereof and a gelling agent which can be used for the treatment of such disorders as pain, inflammation, arthritis, muscle spasm and associated symptoms in humans and animals.

9 Claims, 5 Drawing Sheets

Related U.S. Application Data continuation of application No. 13/463,626, filed on May 3, 2012, now Pat. No. 9,205,041.

(60) Provisional application No. 61/482,058, filed on May 3, 2011.

(51) Int. Cl.
| | | |
|---|---|---|
| *A61K 47/14* | (2017.01) | |
| *A61K 47/10* | (2017.01) | |
| *A61K 47/38* | (2006.01) | |
| *A61K 9/06* | (2006.01) | |
| *A61P 29/00* | (2006.01) | |

(56) References Cited

U.S. PATENT DOCUMENTS

| | | |
|---|---|---|
| 4,849,418 A | 7/1989 | Lohner et al. |
| 4,877,620 A | 10/1989 | Loew et al. |
| 4,916,161 A | 4/1990 | Patell |
| 5,093,133 A | 3/1992 | Wisniewski et al. |
| 5,654,337 A | 8/1997 | Roentsch et al. |
| 5,767,161 A | 6/1998 | Stroppolo et al. |
| 5,807,568 A | 9/1998 | Cody et al. |
| 5,976,566 A | 11/1999 | Samour et al. |
| 6,083,996 A | 7/2000 | Buyuktimkin et al. |
| 2004/0213744 A1 | 10/2004 | Lulla et al. |
| 2005/0032900 A1 | 2/2005 | Krauser ............... A61K 9/0014 514/570 |
| 2007/0071688 A1 | 3/2007 | Illel et al. |
| 2007/0134308 A1 | 6/2007 | Samour et al. |
| 2008/0317684 A1 | 12/2008 | Spann-Wade et al. |
| 2009/0005405 A1 | 1/2009 | Ford |
| 2009/0143762 A1 | 6/2009 | Stinchcomb et al. |
| 2010/0055161 A1 | 3/2010 | Ahn |
| 2010/0074857 A1 | 3/2010 | Lipkin et al. |
| 2010/0273746 A1 | 10/2010 | Balazs et al. |

FOREIGN PATENT DOCUMENTS

| | | |
|---|---|---|
| JP | H11199521 | 7/1999 |
| JP | 2001-513543 | 9/2001 |
| JP | 2008-531693 | 8/2008 |
| JP | 2010-502701 | 1/2010 |
| KR | 20010031828 | 4/2001 |
| WO | 1995/23596 | 9/1995 |
| WO | WO 99/09554 | 3/1999 |
| WO | WO 00/27372 | 5/2000 |
| WO | 2003/028742 | 4/2003 |
| WO | 2005/051347 | 6/2005 |
| WO | WO 2006/096360 | 9/2006 |
| WO | WO 2010/151240 | 12/2010 |
| WO | 2011/063531 | 6/2011 |
| WO | 2011/070318 | 6/2011 |
| WO | 2011/112875 | 9/2011 |

OTHER PUBLICATIONS

Extended European Search Report issued in EP12779275.2 dated Oct. 30, 2014 (13 pages).
Hermes Arzneimittel, Doc © Ibuprofen Schmerzgel 5% Gel (Jul. 2014).
Mercury Pharma Group, Nurofen Ibuprofen 5% Gel Patient Information Leaflet (Nov. 2012).
Office Action issued in Chinese Patent Application No. 201280027488.6 dated Dec. 12, 2014 with English translation (15 pages).
Office Action issued in Colombian Application 13-281.360 dated Dec. 23, 2014 (English translation only) (15 pages).
Office Action issued in New Zealand Application 618259 dated Aug. 4, 2014 (3 pages).
Opposition filed with the Head Office of Inventions and New Technologies of Indecopi, opposing Peruvian patent application No. 2438, dated Oct. 29, 2014 (24 pages, including English translation).
Perioli et al., "Development of mucoadhesive patches for buccal administration of ibuprofen," Journal of Controlled Release, 99(1):73-82 (2004).
The Merck Index, Fifteenth Edition (2013), pp. 905-906.
Opposition brief filed with the Superintendent of Industry and Trade of Colombia, opposing Colombian patent application No. 13-281360, dated May 20, 2014 (14 pages, including English translation).
International Application No. PCT/US12/36366, International Search Report and Written Opinion dated Jul. 30, 2012.
Dinda et al., "Enhancement of skin permeation of ibuprofen from ointments and gels by seasame oil, sunflower oil and oleic acid", Indican Journal of Pharmaceutical Sciences, May-Jun. 2006, pp. 313-316.
English translation of Resolution received in CO13-281.360 dated May 18, 2016 (11 pages).
International Application No. PCT/US12/36366 International Search Report and Written Opinion dated Jul. 30, 2012 (13 pages).
Office Action issued in AU2012250664 dated Jun. 27, 2016 (4 pages).
Office Action issued in CL3163-13 dated Jun. 8, 2016 (14 pages).
Office Action issued in PE2438 dated Sep. 28, 2016 with English translation (16 pages).
Paudel, K.S. et al., "Challenges and opportunities in dermal/transdermal delivery" Therapeutic Delivery, 2010, vol. 1(1), 109-131.
BR Office Action in Brazilian Appln. No. 112013028435, dated May 20, 2019, 4 pages.
EP Search Report in European Appln. No. 19180358.4, dated Sep. 5, 2019, 5 pages.
JP Office Action in Japanese Appln. No. 2014-509451, dated Nov. 13, 2015, 6 pages (English translation).
KR Office Action in Korean Appln. No. 10-2013-7031608, dated May 3, 2018, 5 pages (English translation).
Paudel et al., "Challenges and opportunities in dermal transdermal delivery," Therapeutic Delivery, 2010, 1(1):109-131.

FIG. 2

DESIGN OF EXPERIMENTS (DOE)
3X2 STATISTICAL DESIGN SPACE FOR HPC/WATER/IPA

| | WATER (L) = 0%<br>IPA (H) = 68.0% | WATER (H) = 17.5-20.0%<br>IPA (L) = 45.6-48.0% |
|---|---|---|
| HPC (H) = 2.0% | 001-01(2)<br>SEMI-SOLID GELS | SEMI-SOLID GELS<br>001-03(3*), 003-01(1*)<br>HIGHLY VISCOUS LIQUID<br>003-01(1*) |
| HPC (M) = 1.0% | NOT ATTEMPTED | HIGHLY VISCOUS LIQUID<br>001-05(2) |
| HPC (L) = 0.5% | NOT ATTEMPTED | 001-04(1)<br>VISCOUS LIQUID |

TRANSDERMAL COMPOSITIONS OF IBUPROFEN AND METHODS OF USE THEREOF

CROSS-REFERENCE TO RELATED APPLICATIONS

This application claims the benefit of and is a continuation of U.S. patent application Ser. No. 14/961,172, filed on Dec. 7, 2015, now U.S. Pat. No. 9,849,080, which claims the benefit of and is a continuation of U.S. patent application Ser. No. 13/463,626, filed on May 3, 2012, now U.S. Pat. No. 9,205,041, which claims the benefit U.S. Provisional Application Ser. No. 61/482,058 filed on May 3, 2011, the contents of which are incorporated herein by reference in their entirety.

FIELD OF THE INVENTION

The present invention relates to ibuprofen or salts thereof, particularly the S-enantiomer of ibuprofen, in compositions for transdermal administration. The present invention particularly relates to ibuprofen gel formulations.

INTRODUCTION

Ibuprofen (2-(4-isobutylphenyl)propionic acid) is a common nonsteroidal anti-inflammatory drug (NSAID) for the treatment of pain, inflammation, arthritis, muscle spasm and associated symptoms in humans and animals. Ibuprofen is a racemic mixture of "S" and "R" enantiomers.

Ibuprofen is most commonly administered orally. Topical administration of ibuprofen would offer local and enhanced drug delivery to affected tissues. However, topically administered ibuprofen would penetrate the skin slowly and in small quantities. Overcoming poor penetration of ibuprofen through the skin of humans and animals is a major challenge to transdermal delivery of ibuprofen. There exists a need to provide compositions which are more effective for transdermal delivery of ibuprofen.

BRIEF DESCRIPTION OF THE FIGURE

FIG. 2 is a diagram illustrating the design space showing the relationship between the concentrations of water and hydroxypropyl cellulose (hpc), and the physical state of the formulations (viscous liquid, very viscous liquid or semi-solid).

SUMMARY OF THE INVENTION

Figure 1:
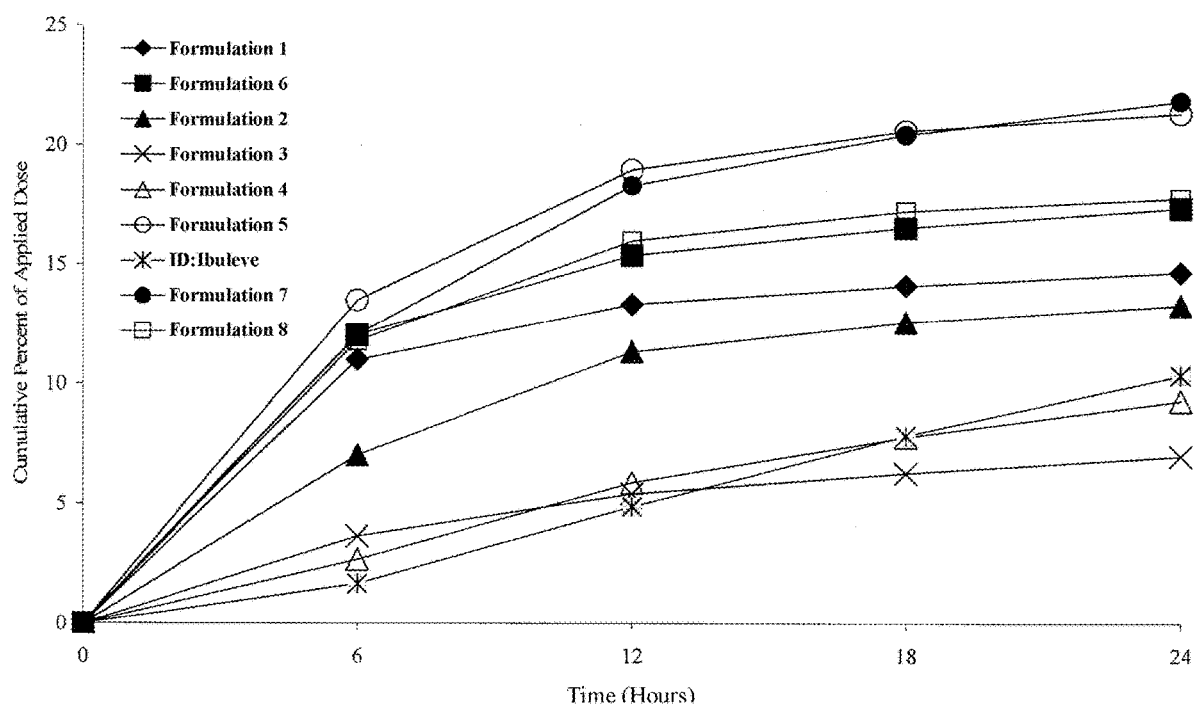
FIG. 1 is a graph illustrating the results from an in vitro 24-hour comparative permeation study of ibuprofen through human skin comparing permeation of different ibuprofen gel formulations of the invention, and a comparative formulation.

In various embodiments, the invention provides transdermal compositions including ibuprofen (2-(4-isobutylphenyl) propionic acid) or salts thereof, a gelling agent and a non-volatile solvent. In other embodiments, the invention provides transdermal gel compositions including ibuprofen, a gelling agent, a lower alkyl glycol, and a lower alkyl alcohol. In further embodiments, the transdermal compositions include one or more skin penetration enhancer(s).

DETAILED DESCRIPTION OF THE INVENTION

As used herein, the terms "formulation" and "composition" are interchangeable.

As used herein, the terms "topical administration," or "transdermal administration," means direct contact, layering or spreading upon dermal tissue, especially outer skin (epidermis) or membrane.

As used herein, all percentages are by weight of the total composition unless otherwise specified.

In certain embodiments, the compositions of the invention are spreadable, semi-solid, gels. The term "gel" as used herein refers to a heterogeneous mixture containing a gelling agent, wherein at least one component is dissolved in a liquid phase.

Ibuprofen useful in accordance with the invention includes the pharmaceutically acceptable salts and esters of ibuprofen, including the racemic mixture comprising the S- and R-enantiomers of ibuprofen, and the substantially pure S-ibuprofen. "Substantially pure S-ibuprofen" means at least 90% by weight S-ibuprofen and 10% or less by weight of the R-enantiomer of ibuprofen, at least 95% by weight S-ibuprofen and 5% or less by weight of the R-enantiomer of ibuprofen, or at least 98% by weight S-ibuprofen and 2% or less by weight of the R-enantiomer of ibuprofen.

Compositions of the invention include ibuprofen in an amount between about 1% and about 30% by weight of the composition. In other embodiments, the compositions comprise ibuprofen in an amount between about 5% to about 20%, between about 5% to about 15%, and between about 8% to about 11% by weight of the composition.

Ibuprofen has poor water solubility due to its relatively lipophilic nature. In view of this, it is important to take into consideration that the blend of ingredients in an ibuprofen composition be capable of dissolving at least 5% by weight ibuprofen at room temperature. In one embodiment, the solubility of ibuprofen in the blend of ingredients of a composition at room temperature is greater than 10% by weight of ibuprofen of the composition. In certain embodiments, the solubility of ibuprofen in the blend of ingredients of a composition at room temperature is greater than 20% by weight. The blend of ingredients of a composition may include a vehicle and optionally one or more other excipients. In certain embodiments, the vehicle comprises a non-volatile solvent and a lower alkyl alcohol. In certain additional embodiments, the vehicle comprises one or more lower alkyl alcohol(s).

The lower alkyl alcohols may be, for example, ethanol, n-propanol, isopropyl alcohol, and mixtures thereof. The compositions may include a lower alkyl alcohol, such as isopropyl alcohol. Further, the compositions may comprise ethanol. In one embodiment, a composition includes more than one lower alkyl alcohol, such as a mixture of ethanol and isopropyl alcohol, for example. A lower alkyl alcohol can be added quantum sufficient, such that the amounts may vary. Typically, a lower alkyl alcohol may be present in a composition in an amount of between about 25% and about 70% by weight of the composition. In certain embodiments, a lower alkyl alcohol may be present in a composition in an amount of between about 35% and about 40%, between about 40% and about 60%, or between 60% and 70% by weight of the composition.

In certain embodiments, compositions may include a non-volatile solvent, such as dimethyl sulfoxide (DMSO), N-methyl pyrrolidone, dimethyl isosorbide, propylene glycol, hexlene glycol and benzyl alcohol. The non-volatile solvent may be present in a composition in an amount of between about 20% and about 60% by weight of the composition, for example. In certain embodiments, a non-volatile solvent may be present in a composition in an amount of between about 30% and about 55%, between about 40% and about 50%, or between 42% and 48% by weight of the composition. In additional embodiments, a composition includes DMSO or N-methyl pyrrolidone in an amount between about 30% and about 55%, between about 40% and about 50%, or between about 42% and about 48% by weight of the composition.

An antioxidant or a chelating agent known in the art may be included in a composition, in particular, when DMSO is present in the composition.

In certain embodiments, a composition may include a non-volatile solvent and one or more lower alkyl alcohol, such as a mixture of DMSO and isopropyl alcohol. In another embodiment, a composition may include a mixture of DMSO, isopropyl alcohol and ethanol.

Compositions may exclude water, such as an anhydrous gel. In other embodiments, the compositions may include water. Typically, when present, the weight percent of water is less than the weight percent of a lower alkyl alcohol in a composition. The compositions may include water in an amount between about 0.1% and about 30% by weight of the composition. In certain embodiments, a composition may include water in an amount between about 0.1% and about 1%, between about 1% and about 5%, between about 5% and about 15%, between about 8% and about 12%, between about 15% and about 30%, or between about 15% and about 25% by weight of the composition.

When water is present in a composition, the composition can have an apparent pH* in the range of 3.0-7.0, more specifically 4.0-5.0.

The compositions may include a gelling agent. Non-limiting examples of suitable gelling agents include carboxyvinyl polymers, methyl cellulose, ethyl cellulose, hydroxycellulose, hydroxyethyl cellulose (HEC), hydroxypropyl cellulose (HPC). An exemplary gelling agent is hydroxypropyl cellulose (KLUCEL® hydroxypropylcellulose manufactured by Hercules, Wilmington, Del.). The gelling agent may comprise a polyacrylic acid polymer (PAA), such as Carbopol polymers which are polymers of acrylic acid cross-linked with polyalkenyl ethers or divinyl glycol. One non-limiting example of a crosslinked polyacrylate polymer is Carbopol® 980 polymer manufactured by Noveon, Inc.

A gelling agent may be present in a composition in an amount, for example, between about 0.1% and about 10% by weight of the composition. In certain embodiments, a composition may include a gelling agent in the amount of between about 1% and about 5%, between about 1.5% and about 3% or between about 3.5% and about 4.5% by weight of the composition.

Compositions of the invention may include a glycol, particularly, a lower alkyl glycol. Non-limiting examples of lower alkyl glycols (i.e., $C_2$ to $C_4$ alkyl glycol) include ethylene glycol, propylene glycol (1,2-propanediol), 1,3-butylene glycol, glycerol, or mixtures thereof. One non-limiting example of a lower alkyl glycol is propylene glycol. The lower alkyl glycol may possess humectant properties and may impart a moisturizing effect to the skin after application. A lower alkyl glycol may in addition or alternatively serve as a vehicle or solvent in the composition. A lower alkyl glycol may be present in an amount of between about 1% and about 40% by weight of the composition. In certain embodiments, a lower alkyl glycol may be present in an amount of between about 5% and about 25%, between about 5% and about 15%, or between about 15% and about 25% by weight of the composition.

A composition may include a skin penetration enhancer (penetration enhancer). A skin penetration enhancer refers to an agent that improves the rate of transport of ibuprofen through the skin surface. A skin penetration enhancer may be present in any amount, such as an amount of between about 0.1% and about 50% by weight of the composition. In certain embodiments, a skin penetration enhancer may be present in an amount of between about 0.1% and about 25%, between about 0.5% and about 10%, or between about 1% and about 5% by weight of the composition. Non-limiting examples of skin penetration enhancers include, sulfoxides such as dimethylsulfoxide (DMSO), ethers such as diethylene glycol monoethyl ether (e.g. Transcutol® P manufactured by Gattefossé, Cedex, France), and surfactants such as sodium laurate, sodium lauryl sulfate, Tween® 20, 40, 60, 80 (manufactured by, Croda Inc, Edison, N.J., U.S.A.); alcohols such as ethanol, propanol, benzyl alcohol; fatty acids such as lauric acid, oleic acid, valeric acid and isostearic acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones. "Percutaneous Penetration Enhancers, eds." Smith et al. (CRC Press, 1995) provides an overview of the field and further background information on enhancers.

The compositions may further include a moisturizer. Non-limiting examples of moisturizers/emollients include, but are not limited to, isopropyl myristate, myristyl lactate, lauryl lactate, glycerin, lanolin, isopropyl palmitate, hexyl laureate, isostearyl alcohol, octyl dodecanol, hexyl decanol, oleyl alcohol, decyl oleate, medium chain triglycerides, linoleic acid and mixtures thereof.

Compositions of the invention may further include an organic base. An organic base may be utilized as an ion-pairing agent in an anhydrous composition. Without being bound by theory, it is hypothesized that inclusion of an organic base results in the formation of complex between the base and the carboxylic acid group of the ibuprofen and limits the ionization potential of the ibuprofen. An organic base may be a primary amine, a secondary amine, or a tertiary amine. Non-limiting examples of organic bases include triethanolamine, diethanolamine, diisopropanolamine, and tromethamine lauramine oxide. In one embodiment, the organic base is triethanolamine.

The amount of base present in a composition may vary. Typically, a base may be present in an amount of between about 0.1% and about 10%, or between about 3% and 8% by weight of the composition.

DMSO containing compositions of the invention may have a viscosity of between about 40,000 cps and about 400,000 cps, or between about 100,000 cps and about 300,000 cps, or between about 150,000 cps and about 250,000 cps. Alcohol based compositions of the invention may have a viscosity of between about 5,000 cps and about 100,000 cps, between about 10,000 cps and about 50,000 cps, or between about 15,000 cps and about 35,000 cps. Low viscosity of the alcohol based compositions (e.g., below about 100,000 cps) may facilitate the spreadability of the compositions. Low viscosity may also result in more rapid diffusion of the ibuprofen within the composition and faster release from the formulation.

The invention also provides methods of producing the ibuprofen compositions described herein. In certain embodiments, a method includes mixing ibuprofen, DMSO, and a gelling agent to yield a gel. A method may further include adding a lower alkyl alcohol and/or a skin penetration enhancer to the gel.

In certain embodiments, a method comprises mixing ibuprofen, a lower alkyl alcohol, a lower alkyl glycol to yield a gel. A method also can include adding a skin penetration enhancer to the gel. In one embodiment, a method includes adding water to the gel, and the pH of the gel is between about pH 4.0 and about pH 5.0.

In certain embodiments, a method comprises mixing ibuprofen, a lower alcohol, a non-volatile solvent and adding the gelling agent as dispersion in hot water, for example, at between 50° C. to 70° C., at between 55° C. to 65° C., or at about 60° C.

In another aspect, the invention provides methods for reducing pain or inflammation comprising administering to a dermal surface of a subject in need of a reduction in pain or inflammation a topical composition of the present invention. The dermal surface may be, for example, the neck, the back, an arm, a hand, a foot, a leg, or a joint. The dermal surface may also be associated with various conditions, for example, lacerations, cuts, bruises, or insect stings. The composition may be applied as needed onto a dermal surface of the subject in an amount sufficient for the ibuprofen to achieve a therapeutically effective concentration to ameliorate the pain or inflammation. The composition can be used for the treatment of pain, inflammation, arthritis, muscle spasm and associated symptoms in humans and animals.

EXAMPLES

The following examples are merely illustrative of the present invention and they should not be considered as limiting the scope of the invention in any way, as these examples and other equivalents thereof will become apparent to those skilled in the art in light of the present disclosure and the accompanying claims. All percentages used in the application are percent weight by weight (w/w) unless otherwise noted.

All ingredients were obtained from commercial vendors. For example, S-(+)-ibuprofen was obtained from Shasun; (R/S)-ibuprofen and propylene glycol NF were obtained from Fisher scientific (Spectrum); isopropyl alcohol NF was obtained from Fisher Scientific (Mallinckrodt); isopropyl myristate NF and triethanolamine NF were obtained from Fisher Scientific; hydroxypropyl cellulose NF (Grade HXF) was obtained from Dow Pharmaceuticals (Ashland); hydroxypropyl cellulose NF (Grade H) was obtained from Nisso (Nippon Soda Co. Ltd.).

Example 1

Preparation of Formulations 1-17

Formulation 1:

A formulation was prepared by mixing the following components.

| Components | % w/w |
|---|---|
| (R/S)-Ibuprofen | 10 |
| Propylene Glycol | 20 |
| Isopropyl Myristate | 5 |
| Hydroxypropyl Cellulose | 2 |
| Isopropyl Alcohol | 63 |

Formulation 2:

A formulation was prepared by mixing the following components.

| Components | % w/w |
|---|---|
| (R/S)-Ibuprofen | 10 |
| Propylene Glycol | 20 |
| Transcutol P | 25 |
| Isopropyl Myristate | 5 |
| Hydroxypropyl Cellulose | 2 |
| Water | 10 |
| Isopropyl Alcohol | 28 |

Formulation 3:

A formulation was prepared by mixing the following components.

| Components | % w/w |
|---|---|
| (R/S)-Ibuprofen | 10 |
| Propylene Glycol | 10 |
| Transcutol P | 10 |
| Isopropyl Myristate | 5 |
| Tween 20 | 2 |
| Hydroxypropyl Cellulose | 2 |
| Benzyl Alcohol | 5 |
| Water | 10 |
| Isopropyl Alcohol | 46 |

Formulation 4:

A formulation was prepared by mixing the following components.

| Components | % w/w |
|---|---|
| (R/S)-Ibuprofen | 10 |
| Propylene Glycol | 20 |
| Isopropyl Myristate | 5 |
| Hydroxypropyl Cellulose | 2 |
| Triethanolamine | 5 |
| Isopropyl Alcohol | 58 |

Formulation 5:

A formulation was prepared by mixing the following components.

| Components | % w/w |
|---|---|
| (R/S)-Ibuprofen | 10.0 |
| Oleic Acid | 2.5 |
| Hydroxypropyl Cellulose | 4.0 |
| Dimethyl Sulfoxide | 45.0 |
| Isopropyl Alcohol | 38.5 |

Formulation 6:

A formulation was prepared by mixing the following components.

| Components | % w/w |
|---|---|
| (R/S)-Ibuprofen | 10 |
| Propylene Glycol | 20 |
| Isopropyl Myristate | 5 |
| Hydroxypropyl Cellulose | 2 |
| Ethanol | 63 |

Formulation 7:

A formulation was prepared by mixing the following components.

| Components | % w/w |
|---|---|
| S-Ibuprofen | 10 |
| Propylene Glycol | 20 |
| Isopropyl Myristate | 5 |
| Hydroxypropyl Cellulose | 2 |
| Isopropyl Alcohol | 63 |

Formulation 8:

A formulation was prepared by mixing the following components.

| Components | % w/w |
|---|---|
| S-Ibuprofen | 10.0 |
| Oleic Acid | 2.5 |
| Hydroxypropyl Cellulose | 4.0 |
| Dimethyl Sulfoxide | 45.0 |
| Isopropyl Alcohol | 38.5 |

Formulation 9:

A formulation was prepared by mixing the following components.

| Components | % w/w |
|---|---|
| Ibuprofen | 10 |
| Propylene Glycol | 10 |
| Isopropyl Myristate | 5 |
| Hydroxypropyl Cellulose | 2 |
| Ethanol (190 Proof) | 73 |

Formulation 10:

A formulation was prepared by mixing the following components.

| Components | % w/w |
|---|---|
| Ibuprofen | 10 |
| Propylene Glycol | 10 |
| Transcutol P | 25 |
| Isopropyl Myristate | 5 |
| Hydroxypropyl Cellulose | 2 |
| Ethanol (190 Proof) | 48 |

Formulation 11:

A formulation was prepared by mixing the following components.

| Components | % w/w |
|---|---|
| Ibuprofen | 10 |
| Propylene Glycol | 10 |
| Isopropyl Myristate | 5 |
| Oleic Acid | 2 |
| Hydroxypropyl Ccellulose | 2 |
| Ethanol (190 Proof) | 71 |

Formulation 12:

A formulation was prepared by mixing the following components.

| Components | % w/w |
|---|---|
| Ibuprofen | 10 |
| Propylene Glycol | 10 |
| Glycerin | 3 |
| Tween 20 | 2 |
| Hydroxypropyl Cellulose | 2 |
| Water | 10 |
| Ethanol (190 Proof) | 63 |

Formulation 13:

A formulation was prepared by mixing the following components.

| Components | % w/w |
|---|---|
| Ibuprofen | 10 |
| Propylene Glycol | 10 |
| Isopropyl Alcohol | 18 |
| Isopropyl Myristate | 5 |
| Hydroxypropyl Cellulose | 2 |
| Ethanol (190 Proof) | 55 |

Formulation 14:

A formulation was prepared by mixing the following components.

| Components | % w/w |
|---|---|
| Ibuprofen | 10 |
| Propylene Glycol | 10 |
| Isopropyl Alcohol | 18 |
| Isopropyl Myristate | 5 |
| Hydroxypropyl Cellulose | 2 |
| Water | 10 |
| Ethanol (190 Proof) | 45 |

Formulation 15:

A formulation was prepared by mixing the following components.

| Components | % w/w |
|---|---|
| Ibuprofen | 10.0 |
| Propylene Glycol | 10.0 |
| Isopropyl Myristate | 5.0 |
| Hydroxypropyl Cellulose | 1.2 |
| Carbopol 980 | 1.2 |
| Ethanol (190 Proof) | 72.6 |

Formulation 16:

A formulation was prepared by mixing the following components.

| Components | % w/w |
|---|---|
| Ibuprofen | 15 |
| Propylene Glycol | 10 |
| Glycerin | 3 |
| Tween 20 | 2 |
| Hydroxypropyl cellulose | 2 |
| Water | 10 |
| Ethanol (190 Proof) | 58 |

Formulation 17:

A formulation was prepared by mixing the following components.

| Components | % w/w |
|---|---|
| Ibuprofen | 20 |
| Propylene glycol | 10 |
| Transcutol P | 25 |
| Isopropyl Myristate | 5 |
| Hydroxypropyl cellulose | 2 |
| Ethanol (190 Proof) | 38 |

Comparative Formulation:

Ibuleve Maximum Strength Gel containing 10% w/w ibuprofen and other ingredients including industrial methylated spirit, carbomers, diethylamine and purified water. Ibuleve is manufactured by DDD Limited, Watford, Herts, WD18 7JJ, UK.

Example 2

In Vitro Skin Permeation Study

Tracer amounts of radiolabeled ($^{14}$C)-R/S-Ibuprofen or ($^{14}$C)-S-Ibuprofen (American Radiolabeled Chemicals, St Louis, Mo.) at approximately 0.50 µCi/dose was added to Formulations 1-8. A single clinically relevant dose (5 mg/cm$^2$) was applied to dermatomed human skin obtained from one single donor following elective surgery.

Percutaneous absorption was evaluated by mounting the dermatomed tissue in Bronaugh flow-through diffusion cells (0.9 cm diameter or 0.64 cm$^2$ area) at 32° C. Six replicates were performed for each formulation. Fresh receptor fluid, PBS containing 0.1% w/v sodium azide and 1.5% (w/v) Oleth-20, pH 7.4, was continuously pumped under the skin at a nominal flow rate of 1.0 mL/hour and collected in 6-hour intervals. Following 24-hours of exposure, the residual formulation remaining on the skin surface was removed by repeated tape stripping (3 strips/cell). Subsequently, the epidermis was physically separated from the dermis by gentle peeling. Tape strips, epidermis and dermis samples were digested using Solune 350 (Perkin Elmer, Chicago, Ill.). The quantity of radioactivity in the tape-strips, epidermis, dermis, and receptor fluid samples was determined using Ultima Gold XR scintillant and a Tricarb 2900TR liquid scintillation counter (Perkin Elmer, Chicago, Ill.). Mass balance was also performed.

The accompanying FIG. 1 is a graph comparing the cumulative quantities (% of applied dose) of ibuprofen diffused through human skin over a 24-hour period of time. The results show formulations 1, 2 and 5-8 have increased transdermal absorption of ibuprofen as compared to the comparative formulation. For example, formulations 5 and 7 provide superior skin permeation of ibuprofen that increased skin permeation of ibuprofen by at least 100% after 24 hours. Formulations 6 and 8 increased skin permeation of ibuprofen by approximately 70% after 24 hours. Formulations 1 and 2 increased skin permeation of ibuprofen by approximately between 20% to 50% after 24 hours. Formulations 3 and 4 exhibit cumulative ibuprofen permeation amounts similar to that of the comparative formulation.

Example 3

Gel Formulations Stability Study

The formulations 1-8 were analyzed for stability of the ibuprofen component at three different temperatures. Each sample of the formulations (16 g) was packaged in a glass scintillation vial and placed at 5° C., 25° C. and 40° C. and a repeated "freeze and thaw" cycles (three cycles). The repeated "freeze and thaw" cycles consisted of storage for 3 or 4 days at −20° C., followed by storage for 3 or 4 calendar days at controlled room temperature of 25° C. The samples were analyzed by reverse phase HPLC with UV detection (220 nm) after 30 days. The percent of the ibuprofen concentration at each time point was determined for the sample formulations. The results are summarized in Table 1 and Table 2.

Appearance and Viscosity of Gel Formulations Study

The physical appearance of the formulations were determined by visual inspection. The viscosity was measured using a Brookfield viscometer for each formulation at the storage conditions described above. The viscosity parameters were specified as follows: (i) chamber 13R, spindle 29, 13 g sample size with a two minute equilibration period prior to measurement, or (ii) chamber 6R, spindle 14, 2.5 g sample size with a two minute equilibration period prior to measurement. The results are summarized in Tables 1 and 2.

TABLE 1

Stability, Appearance and Viscosity of Gel Formulations containing 10% (R/S)-Ibuprofen at 30 days

| Formulation | Storage Condition | Appearance | Viscosity (cps) | (R/S)-Ibuprofen (% LC) |
|---|---|---|---|---|
| 1 | T = 0 | Smooth slightly hazy gel | 28700 | 102.7 |
|  | Freeze/Thaw | Conforms | 32500 | 106.6 |
|  | 5° C. | Conforms | 28550 | 102.8 |
|  | 25° C. | Conforms | 31500 | 101.4 |
|  | 40° C. | Conforms | 30550 | 100.3 |
| 2 | T = 0 | Smooth slightly hazy gel | 30850 | 101.4 |
|  | Freeze/Thaw | Conforms | 30600 | 99.7 |
|  | 5° C. | Conforms | 32850 | 102.3 |
|  | 25° C. | Conforms | 33400 | 100.1 |
|  | 40° C. | Conforms | 31500 | 100.4 |
| 3 | T = 0 | Smooth slightly hazy gel | 27650 | 101.8 |
|  | Freeze/Thaw | Conforms | 28800 | 101.9 |
|  | 5° C. | Conforms | 28000 | 100.7 |
|  | 25° C. | Conforms | 27550 | 100.7 |
|  | 40° C. | Conforms | 26250 | 99.9 |
| 4 | T = 0 | Smooth slightly hazy gel | 29800 | 102.2 |
|  | Freeze/Thaw | Conforms | 33350 | 99.8 |
|  | 5° C. | Conforms | 31700 | 100.9 |
|  | 25° C. | Conforms | 32950 | 100.3 |
|  | 40° C. | Conforms | 30650 | 98.4 |
| 5 | T = 0 | Smooth viscous slightly yellowish gel | 182000 | 101.1 |
|  | Freeze/Thaw | Conforms | 208000 | 100.2 |
|  | 5° C. | Conforms | 219000 | 100.3 |
|  | 25° C. | Conforms | 224000 | 99.9 |
|  | 40° C. | Conforms | 208000 | 101.3 |
| 6 | T = 0 | Smooth slightly hazy gel | 25150 | 101.9 |
|  | Freeze/Thaw | Conforms | 22700 | 101.5 |
|  | 5° C. | Conforms | 21850 | 99.8 |
|  | 25° C. | Conforms | 23450 | 101.4 |
|  | 40° C. | Conforms | 24150 | 97.1 |

TABLE 2

Stability, Appearance and Viscosity of Gel Formulations containing 10% (S)-Ibuprofen at 30 days

| Formulation | Storage Condition | Appearance | Viscosity (cps) | (R/S)-Ibuprofen (% LC) |
|---|---|---|---|---|
| 7 | T = 0 | Smooth slightly hazy gel | 28700 | 101.2 |
|   | Freeze/Thaw | Conforms | 32600 | 101.1 |
|   | 5° C. | Conforms | 30750 | 100.3 |
|   | 25° C. | Conforms | 31250 | 99.7 |
|   | 40° C. | Conforms | 31500 | 99.9 |
| 8 | T = 0 | Smooth viscous slightly yellowish gel | 174000 | 100.5 |
|   | Freeze/Thaw | Conforms | 182000 | 100.7 |
|   | 5° C. | Conforms | 218000 | 101.2 |
|   | 25° C. | Conforms | 195000 | 100.2 |
|   | 40° C. | Conforms | 181000 | 100.4 |

From the results presented above, all formulations exhibited acceptable physical and chemical stability characteristics after 30 days of storage at 5° C., 25° C. and 40° C., and after the repeated "freeze and thaw" cycles (three cycles).

The stability and physical characteristics (appearance and viscosity) of formulation 1 was further studied after 2 months according to the methods described above. The viscosity parameters were: chamber 13R, spindle 29, speed 20 rpm, 13 g sample size with a two minute equilibration period prior to measurement. The results are summarized in Table 3.

TABLE 3

Stability, Appearance and Viscosity of Gel Formulation 1 containing 10% (R/S)-Ibuprofen at 1 and 2 months.

| Storage Condition | Time (Month) | Appearance | Viscosity (cps) | (R/S)-Ibupofen (% LC) | Impurity 1 (Area %) | Impurity 2 (Area %) |
|---|---|---|---|---|---|---|
| N/A | T = 0 | Smooth slightly hazy gel | 28700 | 102.7 | Not Detected | Not Detected |
| Freeze/Thaw | N/A | Conforms | 32500 | 106.6 | Not Detected | Not Detected |
| 5° C. | 1 | Conforms | 28550 | 102.8 | Not Detected | Not Detected |
|   | 2 | Conforms | 32250 | 101.2 | Not Detected | Not Detected |
| 25° C. | 1 | Conforms | 31500 | 101.4 | Not Detected | Not Detected |
|   | 2 | Conforms | 30900 | 101.3 | Not Detected | Not Detected |
| 40° C. | 1 | Conforms | 30550 | 100.3 | 0.70 (RRT = 1.07) | 0.12 (RRT = 1.09) |
|   | 2 | Conforms | 31800 | 96.5 | 0.70 (RRT = 1.07) | 0.12 (RRT = 1.09) |

From the results presented above, formulation 1 exhibited acceptable physical and chemical stability characteristics after 1 and 2 months of storage at 5° C., 25° C. and 40° C., and after the repeated "freeze and thaw" cycles (three cycles).

Example 4

Solubility of Ibuprofen in Solvents and Solvent Blends

Excess Ibuprofen was equilibrated overnight (>16 hr) at room temperature in various solvents and solvent blends. The solubility of ibuprofen was assessed visually. The solubility of ibuprofen results are shown in Tables 4 and 5.

TABLE 4

S-Ibuprofen Solubility at Room Temperature

| Solvents | S-Ibuprofen Solubility (% w/w) |
|---|---|
| Propylene glycol | >23 |
| Benzyl alcohol | >23 |
| Ethanol | >23 |
| Hexylene glycol | >23 |
| PEG 400 | >23 |
| Isopropyl alcohol | >23 |
| Transcutol P | >23 |
| Dimethyl isosorbide | >20 |
| Diethyl sebacate | >23 |
| Isopropyl myristate | >16 |
| Myristyl lactate | 4.7-9.1 |
| Isostearyl alcohol | <4.8 |
| Isostearic acid | <4.8 |
| Octyldodecanol | <4.8 |

TABLE 5

(R/S) Ibuprofen and S-Ibuprofen Solubility in Solvent Blends at RT

| Solvents (% w/w) | Solvent Blend No. | | | | | |
|---|---|---|---|---|---|---|
|   | 1 | 2 | 3 | 4 | 5 | 6 |
| Propylene glycol | 10 | 10 | 10 | 10 | 10 | 10 |
| Glycerin | 3 | — | — | — | — | — |
| Tween 20 | 2 | — | — | — | — | — |
| Transcutol P | — | 25 | — | — | — | — |
| Isopropyl myristate | — | 5 | 25 | 15 | 5 | 5 |
| Water | 10 | — | — | — | 10 | — |
| Isopropyl alcohol | — | — | — | 18 | 18 | — |
| Ethanol | 63 | 38 | 43 | 35 | 35 | 73 |
| Solubility |   |   |   |   |   |   |
| Solubility of (R/S) Ibuprofen (% w/w) | >20 | >20 | >20 | >20 | >20 | >20 |
| Solubility of S-Ibuprofen (% w/w) | >20 | >20 | >20 | >20 | >20 | >20 |

The results in Table 4 indicate that the solubility of both (R/S) Ibuprofen and S-Ibuprofen are greater than 20% w/w at room temperature in all solvent blends tested.

Example 5

Preparation of Formulations 18-24

| Formulation 18: | | |
|---|---|---|
| Components | % w/w | Amount |
| (R/S)-Ibuprofen | 5 | 12.5 g |
| Propylene Glycol | 20 | 48.3 mL |
| Isopropyl Myristate | 5 | 14.7 mL |
| Hydroxypropyl Cellulose | 2 | 5.0 g |
| Isopropyl Alcohol | 68 | 217.7 mL |

| Formulation 19: | | |
|---|---|---|
| Components | % w/w | Amount |
| (R/S)-Ibuprofen | 5 | 12.5 g |
| Propylene Glycol | 20 | 48.3 mL |
| Isopropyl Myristate | 5 | 14.7 mL |
| Hydroxypropyl Cellulose | 2 | 5.0 g |
| Isopropyl Alcohol | 68 | 217.7 mL |
| Water | 20 | 50.0 mL |

| Formulation 20: | | |
|---|---|---|
| Components | % w/w | Amount |
| (R/S)-Ibuprofen | 5 | 12.5 g |
| Propylene Glycol | 20 | 48.3 mL |
| Isopropyl Myristate | 5 | 14.7 mL |
| Hydroxypropyl Cellulose | 0.5 | 1.25 g |
| Isopropyl Alcohol | 49.5 | 158.5 mL |
| Water | 20 | 50.0 mL |

| Formulation 21: | | |
|---|---|---|
| Components | % w/w | Amount |
| (R/S)-Ibuprofen | 5 | 12.5 g |
| Propylene Glycol | 20 | 48.3 mL |
| Isopropyl Myristate | 5 | 14.7 mL |
| Hydroxypropyl Cellulose | 1 | 2.50 g |
| Isopropyl Alcohol | 49.0 | 156.9 mL |
| Water | 20 | 50.0 mL |

| Formulation 22: | | |
|---|---|---|
| Components | % w/w | Amount |
| (R/S)-Ibuprofen | 5 | 12.5 g |
| Propylene Glycol | 20 | 48.3 mL |
| Isopropyl Myristate | 5 | 14.7 mL |
| Hydroxypropyl Cellulose | 2 | 5.0 g |
| Triethanolamine | 5 | 11.2 mL |
| Isopropyl Alcohol | 45.5 | 145.7 mL |
| Water | 17.5 | 43.8 mL |

| Formulation 23: | | |
|---|---|---|
| Components | % w/w | Amount |
| (R/S)-Ibuprofen | 10 | 25 g |
| Propylene Glycol | 20 | 48.3 mL |
| Isopropyl Myristate | 5 | 14.7 mL |
| Hydroxypropyl Cellulose | 2 | 5.0 g |
| Isopropyl Alcohol | 45.5 | 145.7 mL |
| Water | 17.5 | 43.8 mL |

| Formulation 24: | | |
|---|---|---|
| Components | % w/w | Amount |
| S-Ibuprofen | 5 | 12.5 g |
| Propylene Glycol | 20 | 48.3 mL |
| Isopropyl Myristate | 5 | 14.7 mL |
| Hydroxypropyl Cellulose | 2 | 5.0 g |
| Isopropyl Alcohol | 48 | 153.7 mL |
| Water | 20 | 50.0 mL |

Formulations 18-24 were prepared according to one of the three manufacturing processes I, II and III, as described below.

Manufacturing Process I: Ibuprofen was dissolved in isopropyl alcohol followed by addition of the remaining liquid ingredients. The solution was mixed by stirring using a magnetic stir bar. The solution was maintained at room temperature (e.g. ~22° C.), and hydroxypropyl cellulose was then added with stirring using an overhead paddle stirrer.

Manufacturing Process II: This process was carried out as described in Process I except that the temperature of the mixture was maintained at 60° C. throughout.

Manufacturing Process III: Ibuprofen was dissolved in the organic solvents at 60° C. Hydroxypropyl cellulose was dispersed in water at 60° C. and stirred with a magnetic stirrer for about 10 minutes to produce a fine dispersion free of large particles. The hydroxypropyl cellulose dispersion was then added slowly to the ibuprofen solution with a stirring using an overhead paddle stirrer. The resultant formulation was then stirred for approximately 10-15 minutes at 1,000-1,500 rpm until the hydroxypropyl cellulose was completely dissolved.

Manufacturing Process II was used to prepare Batch 2 of Formulation 18 and Batch 1 of Formulation 21.

Manufacturing process I was used to prepare Batch 1 of Formulation 18. The addition of hydroxypropyl cellulose to the ibuprofen solution at room temperature (~22° C.) resulted in incomplete dissolution of hydroxypropyl cellulose. A significant amount of undissolved, partially solvated particles of hydroxypropyl cellulose was observed even after stirring of the mixture for 30 min at 2,000 rpm. Complete dissolution of hydroxypropyl cellulose into the formulation at room temperature was achieved by storage for 1 hour in the refrigerator (~5° C.), and subsequently 5 hours at room temperature (~22° C.) followed by manual shaking at room temperature for 30 min.

Manufacturing process II was used to prepare Batch 2 of Formulation 18. The rate and extent of the dissolution of hydroxypropyl cellulose was improved but remained incomplete by adding hydroxypropyl cellulose at elevated temperature (e.g., 60° C.). Complete dissolution of hydroxypropyl cellulose into the formulation was achieved more readily according to manufacturing process I by manual shaking as the formulation cooled to room temperature.

Several attempts to prepare Formulation 18 by first dispersing hydroxypropyl cellulose in isopropyl alcohol at 60° C. were made. However, due to the rapid gelling of the resulting mixtures, such attempts were unsuccessful.

Manufacturing process II was also used to prepare Batch 1 of Formulation 21.

Manufacturing process III was used to prepare formulations containing 20% water, e.g., Formulations 19, 20, 22, 23, 24 and batch 2 of Formulation 21.

Example 6

Visual Inspection

The results of the visual inspection of the Formulations prepared in Example 5 are provided in Table 6.

Formulation 21 prepared by manufacturing process I (Batch 1) was slightly hazy and contained a few translucent particles ("fish-eyes"). Yet, the fish-eyes in Formulation 21 Batch 1 disappeared after standing for approximately 72 hours at room temperature.

Example 7

The effects of the concentrations of water, ibuprofen concentration (5% or 10%), ibuprofen stereochemistry (S- vs. R,S-forms), HPC (0.5%, 1.0% or 2.0%), IPA (45.5%-68.0%) and TEA concentration (0% or 5%) are described below.

TABLE 6

Visual Appearance and Apparent pH* Values of the Batches of Ibuprofen Topical Gels, Initially and after 24 Hours at Room Temperature

| | Formulation | | | | | | | | | |
|---|---|---|---|---|---|---|---|---|---|---|
| | 18 | | 19 | | 20 | 21 | | 22 | 23 | 24 |
| Batch | 1 | 2 | 1 | 2 | 1 | 1 | 2 | 1 | 1 | 1 |
| Manufacturing Process | I | II | III | III | III | II | III | III | III | III |
| API | | | | | | | | | | |
| R,S-Ibuprofen USP (%) | 5.0 | 5.0 | 5.0 | 5.0 | 5.0 | 5.0 | 5.0 | 5.0 | 10.0 | — |
| S-Ibuprofen (%) | — | — | — | — | — | — | — | — | — | 5.0 |
| Excipients | | | | | | | | | | |
| Propylene Glycol NF (%) | 20.0 | 20.0 | 20.0 | 20.0 | 20.0 | 20.0 | 20.0 | 20.0 | 20.0 | 20.0 |
| Isopropyl Myristate NF (%) | 5.0 | 5.0 | 5.0 | 5.0 | 5.0 | 5.0 | 5.0 | 5.0 | 5.0 | 5.0 |
| Triethanolamine NF (%) | — | — | — | — | — | — | — | 5.0 | — | — |
| Thickening Agents | | | | | | | | | | |
| Hydroxypropyl Cellulose (Klucel HXF) (%) | 2.0 | 2.0 | 2.0 | — | 0.5 | 1.0 | 1.0 | 2.0 | 2.0 | 2.0 |
| Hydroxypropyl Cellulose (Nisso H) (%) | — | — | — | 2.0 | — | — | — | — | — | — |
| Solvents | | | | | | | | | | |
| Water (%) | — | — | 20.0 | 20.0 | 20.0 | 20.0 | 20.0 | 17.5 | 17.5 | 20.0 |
| Isopropyl Alcohol NF (%) | 68.0 | 68.0 | 48.0 | 48.0 | 49.5 | 49.0 | 49.0 | 45.5 | 45.5 | 48.0 |
| Apparent pH* | 4.3-4.4$^x$ | 4.4-4.5$^x$ | 4.10 | 3.95 | 3.77 | 3.59 | 3.87 | 8.04 | 4.13 | 4.15 |
| Observation Initially | | | | | | | | | | |
| Clarity | H | H | H | Cl | Cl | SH | Cl | SH | SH | SH |
| Particles | ++ | + | − | − | + | + | − | − | − | − |
| Fish Eyes | ++ | + | − | − | + | + | − | − | − | − |
| Thickness | SS | SS | SS | HVL | VL | VVL | VVL | SS | SS | SS |
| After 24 Hours | | | | | | | | | | |
| Clarity | H | | H | Cl | SH | SH | Cl | SH | SH | SH |
| Particles | − | | − | − | + | +/− | − | − | − | − |
| Fish Eyes | +/− | | − | − | + | +/− | − | − | − | − |
| Thickness | SS | | SS | HVL | VL | HVL | HVL | SS | SS | SS |

*Due to the completely non-aqueous nature of these formulations, the pH* value fluctuated within a range.
Clarity: Cl = clear, SH = slightly hazy, H = hazy, VH = very hazy, Cd = cloudy
Thickness: VL = viscous liquid, HVL = highly viscous liquid, SS = semi-solid All formulations prepared by manufacturing process III were free of visible particles, and appeared to be either slightly hazy or hazy at the completion of the formulation preparation and after 24 hours of standing at room temperature. Formulation 21 prepared by manufacturing process III (Batch 2) was free of visible particles and clear. However, Effects of Concentrations of Hydroxypropyl Cellulose and Water A partial 3×2 statistical design of experiments (DOE) was conducted to determine the effects of hydroxypropyl cellulose concentration and water concentration on the visual appearance and the thickness of the formulations prepared in Example 5 (See FIG. 2). Two levels of water concentration (low, L=0%, high, H=20%) and three levels of hydroxypropyl cellulose (HPC) (low, L=0.5%, mid, M=1.0%, high, H=2.0%) concentration were explored in the design.

The formulations were classified qualitatively as a "viscous liquid" (VL, free-flowing), a "highly viscous liquid" (HVL, slow-flowing) or a "semi-solid" (SS, nonflowing), according to the principles in the topical drug decision tree published by the FDA in 2005, L. Buhse et al. Topical Drug Classification, Int. J. Pharm. 295, 101-112 (2005).

FIG. 2 shows all formulations containing 2% HPC (Klucel Grade HXF) with either 0% or about 20% water were semi-solid at room temperature. Formulations containing 0.5% or 1% HPC with about 20% water were viscous or highly viscous liquids, respectively. Although the viscosities of the formulations were not measured quantitatively, the formulations free of water appeared stiffer in consistency and requiring more force to spread them over a flat surface than those containing 20% water. In addition to controlling the thickness of the formulation, the concentration of HPC also affected the visual appearance, with the degree of haze increasing with increasing concentration of HPC.

Replacement of HPC (Klucel Grade HXF, MW: 1.15 MDa) with a slightly lower molecular weight HPC (Nisso Grade H, MW: 910 mD), produced a highly viscous liquid (cf. a semi-solid gel), demonstrating that both the molecular weight and the concentration of HPC are important variables in determining the form of the gel (liquid vs. semi-solid).

Effects of Triethanolamine

The effects of triethanolamine was studied by comparing the visual appearance of Formulations 22 and 19. Formulation 22 contains 5% triethanolamine and is the closest in composition to Formulation 19 which contains the same concentrations of R,S-ibuprofen (5%), isopropyl myristate (5%), hydroxypropyl cellulose (2%), and slightly lower concentrations of isopropyl alcohol (45.5% vs. 48.0%) and water (17.5% vs. 20.0%). Formulations 22 and 19 were visually indistinguishable where both were semi-solid gels that could be spread easily across a flat surface. Formulation 22 contains 5% triethanolamine was somewhat less hazy than the Formulation 19. These results indicated the inclusion of 5% triethanolamine has very little effect on the visual appearance and thickness of the ibuprofen gels prepared.

Effects of Ibuprofen Concentration

Formulation 23 contains 10% (R,S)-ibuprofen and is the closest in composition to Formulation 19, which contains 5% R,S-ibuprofen, the same concentrations of IPM (5%), HPC (2%), and slightly lower concentrations of IPA (45.5% vs. 48.0%) and water (17.5% vs. 20.0%). Both Formulations 23 and 19 were semi-solid gels that could be spread easily across a flat surface. These results indicate the concentration of ibuprofen in the range 5-10% has very little effect on the visual appearance or thickness of the ibuprofen gels prepared in this study.

Effects of Stereochemistry of Ibuprofen

Formulations 19 and 24 were identical in excipient composition and differed only in the stereochemistry of the drug substance. Formulations 19 and 24 contain 5% (R,S)- and 5% (S)-ibuprofen, respectively. The results (Table 2) indicate the stereochemistry of ibuprofen (R,S vs. S) has very little effect on the visual appearance or the thickness of the ibuprofen gels prepared in this study.

Effects of Apparent pH* Values

With the exception of Formulation 22, the apparent pH* values of the formulations ranged between 3.59 (Formulation 21) and 4.50 (Formulation 18), consistent with the presence of 5-10% ibuprofen, which is a weak acid. The higher apparent pH* value of Formulation 22 can be attributed to the presence of 5% triethanolamine, which is also a weak base.

Conclusions

For topical gels based on formulations containing fixed concentrations of propylene glycol (20.0%), isopropyl myristate (5.0%), and varying concentrations of hydroxypropyl cellulose (0.5%, 1.0%, 2.0%), isopropyl alcohol (45.5%-68.0%), water (0%-20.0%), triethanolamine (0, 5.0%) and either R,S-ibuprofen (5.0% or 10.0%) or S-ibuprofen (5.0%), the following conclusions can be drawn.

All formulations prepared with 2.0% hydroxypropyl cellulose (Klucel HXF) and either 5.0% or 10.0% ibuprofen (S-, or R,S-) were semi-solid gels at room temperature.

Replacement of Klucel HXF with the same concentration (2.0%) of the highest molecular weight grade (H) of hydroxypropyl cellulose from Nisso produced a highly viscous liquid rather than a semi-solid gel.

Whereas all formulations containing 2% Klucel hydroxypropyl cellulose (Grade HXF) were semi-solid gels, those formulations containing 20.0% water could be spread more easily across a flat surface (suggesting a lower viscosity of the gel).

There were no meaningful effects of the concentration of R,S-ibuprofen (5.0% vs. 10.0%), the stereochemical form of ibuprofen (5.0% S- vs. 5.0% R,S-) or the addition of 5.0% triethanolamine on the visual appearance or the thickness of the gels. Additionally, the clarity of the gels stored at room temperature for periods longer than 24 hours improved over time and the differences in the clarity of the various formulation became less obvious.

Formulations containing 20% water can be prepared using a two-vessel method (according to manufacturing process III), in which the ibuprofen is dissolved in the liquid excipients in a first vessel, and hydroxypropyl cellulose is dispersed in water at 60° C. in a second vessel. The content of the second vessel is then added to the content of the first vessel containing the ibuprofen solution.

Formations containing no added water can be prepared in a single vessel by first dissolving the ibuprofen in the solvents and then adding the hydroxypropyl cellulose directly to the ibuprofen solution. Heating the mixture to 60° C. increased the rate and the extent of dissolution of hydroxypropyl cellulose. However, complete dissolution of the hydroxypropyl cellulose in the ibuprofen gels containing no added water prepared at room temperature required storage at room temperature for 48 hours followed by shaking for 30 minutes. Complete dissolution of hydroxypropyl cellulose in the ibuprofen gels containing no added water prepared at 60° C. required shaking for 30 minutes required shaking as the gel cooled to room temperature.

Example 8

Determination of "Pharmaceutical Elegance" of Formulations

Various physical appearances and characteristics such as clarity (Cl), color (C), particulates (P), thickness (T), odor (O), residue (R) and acceptability (A) are viewed as components of pharmaceutical elegance of the topical formulations, and they were evaluated for ten formulations including formulations 9, 18, 19 and 21-24 prepared in the previous examples and three commercial formulations: Neurofen Ibuprofen 5% Gel, DOC Ibuprofen 5% Gel and Boots Ibuprofen 5% Gel.

The physical appearances of the formulation samples were examined by human eyes one sample at a time, where each sample was placed in a clear vial against a white background based on the following rating scales:

Clarity (Cl): Clear=5; Slightly Hazy=4; Hazy=3; Very Hazy=2; Cloudy=1

Color (C) Colorless=5; Faint Yellow=4; Slightly Yellow=3; Yellow=2; Intense Yellow=1

Particulates (P) (vials were kept upright and rotated through 360 degree): no visible particles=5; a few translucent "fish-eyes" (solvated hydroxypropyl cellulose particles)=4; several very noticeable "fish eyes"=3; many "fish eyes" and a few white particles (undissolved hydroxypropyl cellulose)=2; many large translucent lumps and white particles=5

Thickness (T) (vials were turned slowly upside down and observed the rate of gel falling from the bottom of the vial): semi solid (stays in place or falls as a lump)=5; highly viscous liquid (flows very slowly)=4; viscous liquid (flows slowly)=3; slightly viscous (flows quickly)=2; free flowing liquid (flows immediately)=1

Odor (O): odorless=5; faint odor=4; very noticeable odor=3; strong odor=2; strong, unpleasant odor=1

Residue on drying (R): none=5; slightly sticky=4; sticky with slight residue=3; sticky with significant residue=2; very sticky with stringy residue=1

Pharmaceutical elegance scores including both unweighted (PE) and weighted (PE') scores, were calculated from the following equations:

$$PE = (P + Cl + C + T + O + R) \quad (1)$$

$$PE' = PE \times A \quad (2)$$

where A is a weighting factor assessed on the overall acceptability of the formulations (A=2 acceptable, A=1 marginally acceptable, A=0 unacceptable). The rating of A is a subjective assessment based on prior experience with gels.

The results of the visual inspection of the physical appearances and characteristics, and the calculated unweighted (PE) and weighted (PE') pharmaceutical elegance are provided in Table 7.

TABLE 7

Assigned Values of Physical Appearances or Characteristics (Clarity, Color, Odor, Thickness, Residue and Acceptabiltiy) and Calculated Unweigted (PE) and Weighted (PE') Pharmaceutical Elegance Scores of the Formulations

| | Formulations | | | | | | | | | |
|---|---|---|---|---|---|---|---|---|---|---|
| | 21 | 8 | 19 | Neurofen | 23 | 24 | Boots | 22 | DOC | 18 |
| API | | | | | | | | | | |
| R,S-Ibuprofen US | 5.0 | — | 5.0 | 5.0 | 10.0 | — | 5.0 | 5.0 | 5.0 | 5.0 |
| S-Ibuprofen | — | 10.0 | — | — | — | 5.0 | — | — | — | — |
| Excipients | | | | | | | | | | |
| Propylene Glycol NF (%) | 20.0 | — | 20.0 | — | 20.0 | 20.0 | — | 20.0 | — | 20.0 |
| Isopropyl myristate NF (%) | 5.0 | — | 5.0 | — | 5.0 | 5.0 | — | 5.0 | — | 5.0 |
| Oleic Acid NF (%) | — | 2.5 | — | — | — | — | — | — | — | — |
| DMSO, USP (%) | — | 45.0 | — | — | — | — | — | — | — | — |
| Dimethylisosorbide (%) | — | — | — | — | — | — | Unk[1] | — | — | — |
| Benzyl Alcohol (%) | — | — | — | 1.0 | — | — | — | — | Unk[1] | — |
| Triethanolamine NF (%) | — | — | — | — | — | — | — | 5.0 | — | — |
| Thickening Agents | | | | | | | | | | |
| Poloxamer (%) | — | — | — | Unk[1,2] | — | — | Unk[1] | — | — | — |
| Ethylhydroxy cellulose (%) | — | — | — | Unk[1,2] | — | — | — | — | Unk[1] | — |
| Hydroxypropyl cellulose NF (Kucel HXF) (%) | 1.0 | 4.0 | 2.0 | Unk[2] | 2.0 | 2.0 | — | 2.0 | — | 2.0 |
| Diluents | | | | | | | | | | |
| Water (%) | 20.0 | — | 20.0 | Unk[1] | 17.5 | 20.0 | Unk[1] | 17.5 | Unk[1] | — |
| Isopropyl Alcohol NF (qs) (%) | 49.0 | 38.5 | 48.0 | — | 45.5 | 48.0 | Unk[1] | 45.5 | Unk[1] | 68.0 |

Pharmaceutical Elegance

| | Formulations | | | | | | |
|---|---|---|---|---|---|---|---|
| | 21 | 8 | 19 | 23 | 24 | 22 | 18 |
| Clarity (1-5) | 3 | 3 | 4 | 5 | 3 | 4 | 5 | 4 | 5 | 3 |
| Color (1-5) | 5 | 4 | 5 | 5 | 4 | 5 | 5 | 5 | 5 | 5 |
| Particulates (1-5) | 4 | 4 | 4 | 5 | 3 | 4 | 5 | 4 | 3 | 4 |
| Thickness (1-5) | 1 | 5 | 4 | 3 | 4 | 4 | 5 | 4 | 2 | 5 |
| Odor (1-5) | 2 | 2 | 4 | 4 | 3 | 3 | 2 | 3 | 4 | 3 |

TABLE 7-continued

Assigned Values of Physical Appearances or Characteristics (Clarity, Color, Odor, Thickness, Residue and Acceptabiltiy) and Calculated Unweigted (PE) and Weighted (PE') Pharmaceutical Elegance Scores of the Formulations

| | | | | | | | | | | |
|---|---|---|---|---|---|---|---|---|---|---|
| Residue (1-5) | 4 | 2 | 4 | 5 | 3 | 5 | 4 | 5 | 5 | 5 |
| Acceptability (0, 1, 2) | 0 | 0 | 2 | 2 | 1 | 2 | 1 | 2 | 1 | 1 |
| Unweighted Score | 19 | 20 | 25 | 27 | 20 | 25 | 26 | 25 | 24 | 25 |
| Weighted Score (PE) | 0 | 0 | 50 | 54 | 20 | 50 | 26 | 50 | 24 | 25 |

[1]Concentration of excipients in commercial products not available
[2]Thickening agent in Neurofen unknown Results and Discussion The unweighted pharmaceutical elegance scores (PE) were calculated and ranked for the formulations from highest (i.e., most desirable) to lowest (i.e., least desirable) as follows:
Neurofen 5% Ibuprofen Gel (PE=27)
Boots 5% Ibuprofen Gel (PE=26)
Formulation 18 (PE=25)
Formulation 19R (PE=25)
Formulation 24 (PE=25)
Formulation 22 (PE=25)
DOC 5% Ibuprofen Gel (PE=24)
Formulation 23 (PE=20)
Formulation 8 (PE=20)
Formulation 21 (PE=19)

Figure 3:
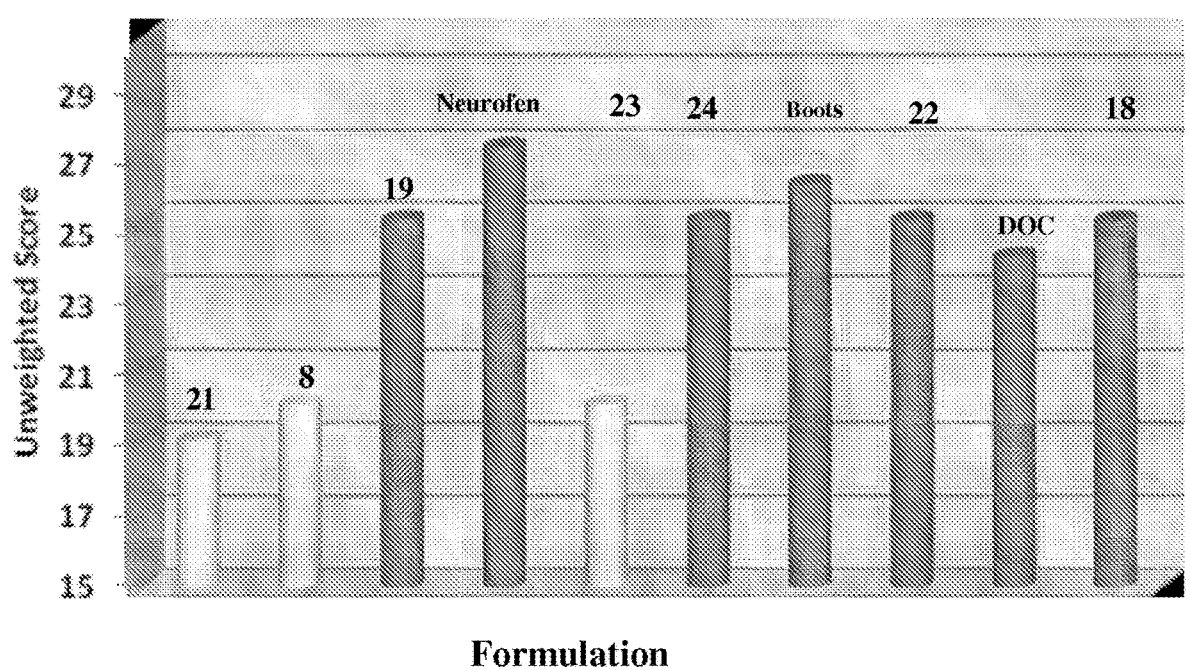
FIG. 3 is a diagram illustrating the unweighted pharmaceutical elegance scores.

The unweighted pharmaceutical elegance scores are further summarized in FIG. 3.

It is noted that the presence of 5% ethanolamine (Formulation 22) or the replacement of R,S-ibuprofen with the S-enantiomer did not change the unweighted PE score (25/30). The lower PE score of 20/30 for Formulation 23 which contains 10% ibuprofen (other formulations contain 5% ibuprofen) was due to the combination of slightly lower score for clarity (3/5), particulates (3/5), odor (3/5) and residue (3/5). The lower PE score (20/30) for Formulation 8 based on DMSO and oleic acid was attributed mainly to the low scores for odor (2/5) and residue (2/5). The lowest PE score (19/30) for Formulation 21 was due to the low scores for thickness (1/5) and odor (2/5).

All formulations studied were designed to be semi-solid gels, except for Formulation 21 which was a free-flowing liquid.

The weighted pharmaceutical elegance scores (PE') were calculated and ranked for the formulations (highest [most desirable] to lowest [least desirable]) as follows:
High (PE'=50-54)
Neurofen 5% Ibuprofen Gel (A=2, PE'=54)
Formulation 19 (A=2, PE'=50)
Formulation 24 (A=2, PE'=50)
Formulation 22 (A=2, PE'=50)
Medium (PE'=20-26)
Boots 5% Ibuprofen Gel (A=1, PE'=26)
Formulation 18 (A=1, PE'=25)
DOC 5% Ibuprofen Gel (A=1, PE'=24)
Formulation 23 (A=1, PE'=20)
Low (PE'=0)
Formulation 21 (PE'=0)
Formulation 8 (PE'=0)

Figure 4:
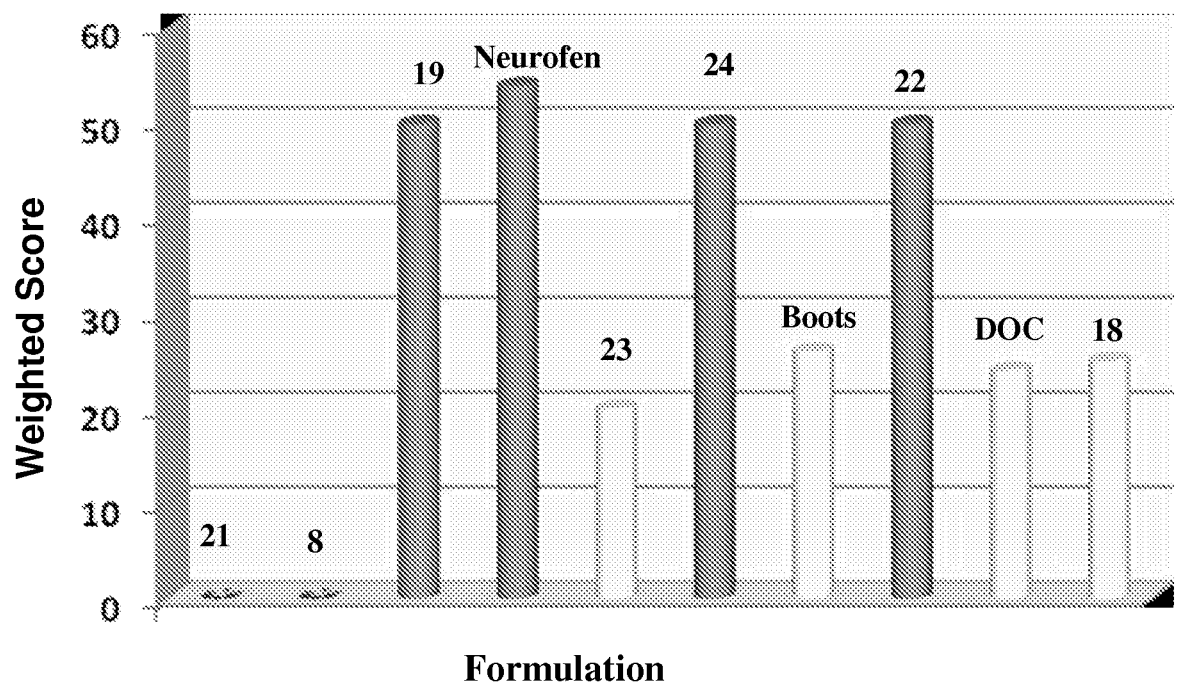
FIG. 4 is a diagram illustrating the weighted pharmaceutical elegance scores.
Figure 5:
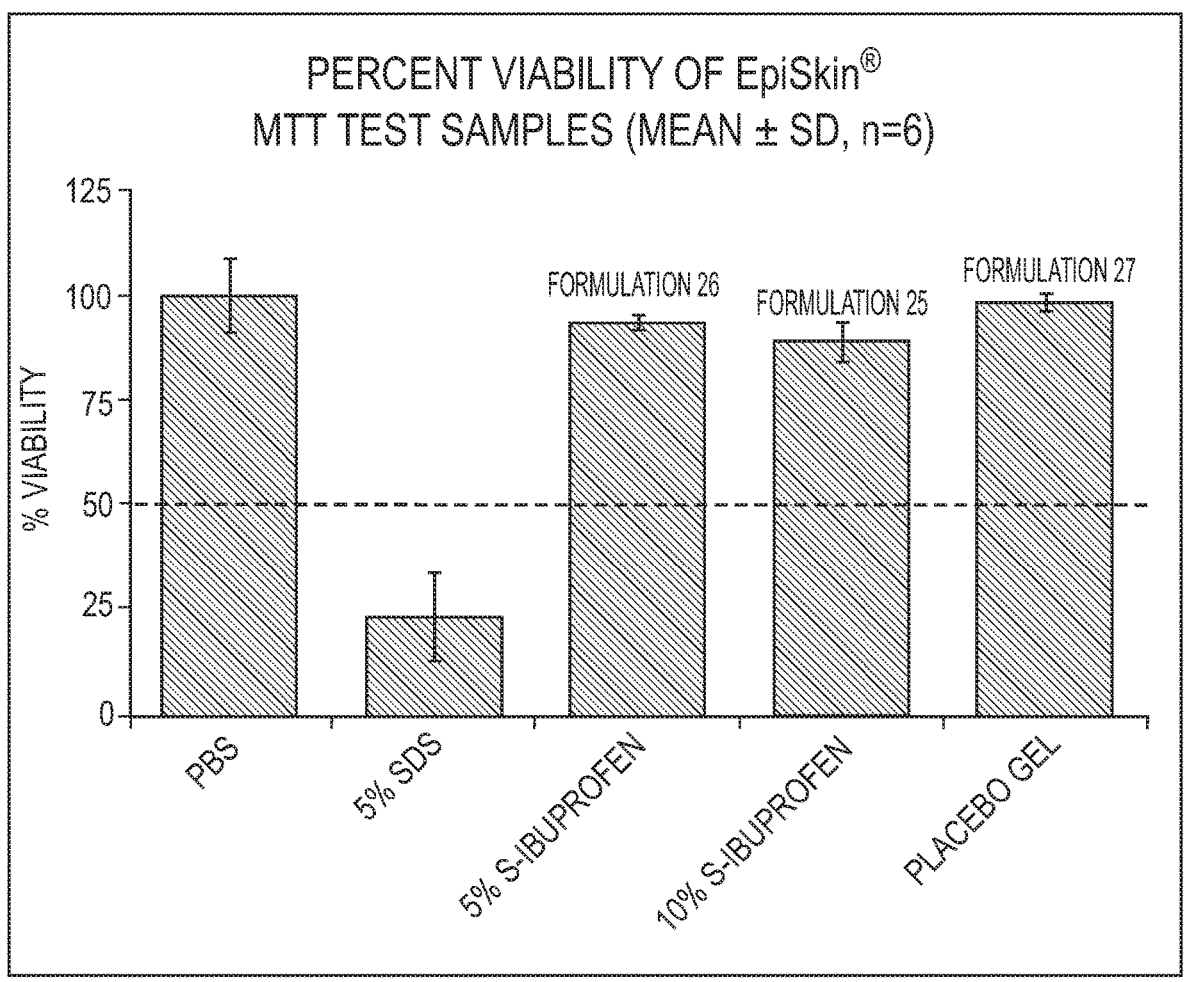
FIG. 5 is a diagram illustrating the Percent Viability of EpiSkin® MTT Test samples (Mean SD, n=6).

The weighted pharmaceutical elegance scores are further summarized in FIG. 4.

The intermediate weighted pharmaceutical elegance scores assigned to the two commercial formulations (DOC and Boots, 5% Ibuprofen Gels), and Formulations 18 and 23 can be attributed primarily to the following factors: DOC 5% Ibuprofen Gel: the presence of particulates and fast flowing nature; Boots 5% Ibuprofen Gel: a strong odor and slightly sticky nature; Formulations 18 and 23: hazy, thick gels with/without a sticky residue.

The low weighted pharmaceutical elegance scores for Formulation 21 can be attributed to the free-flowing liquid form. The low score for Formulation 8 can be attributed to the high thickness and potentially more difficult to spread, it was also sticky and easily leave a significant residue behind after application.

Conclusions

Of the six prepared formulations of the study, three of the formulations 19, 22 and 24 provided excellent Pharmaceutical Elegance and compared very favorably with the commercial formulation (Neurofen 5% Ibuprofen Topical Gel) (Diagram 3). The components common to all three of the formulations disclosed are 5% ibuprofen (R,S- or S-), 5% hydroxypropyl cellulose and 20% water. Inclusion of 5% triethanolamine did not appear to alter the pharmaceutical elegance and may provide some additional benefits from a skin permeability perspective.

Formulations 18 and 23 contain either no water or 10% R,S-ibuprofen, respectively, were considered acceptable and compared favorably with the other two commercial formulations DOC and Boots 5% Ibuprofen Gels.

The Pharmaceutical Elegance of Formulation 8 containing DMSO/oleic acid was marginal.

Example 9

In Vitro Dermal Irritation EpiSkin Test

The potential for skin irritation of two different concentrations of S-ibuprofen formulations and a placebo (vehicle control) were evaluated in a in vitro dermal irritation EpiSkin (reconstructed human epidermis) test. The SkinEthic EpiSkin® test system has been validated by OECD test method (439) as an in vitro model to assess skin irritation potential. The test uses human keratinocytes derived from healthy donors, grown in vitro to reconstruct a functional model of the human epidermis.

Formulations 25-27 were prepared according to the manufacturing process II as described in Example 5 and the contents of the formulations are listed below.

| Formulation 25: | |
|---|---|
| Components | % w/w |
| S-Ibuprofen | 10 |
| Propylene Glycol | 20 |
| Isopropyl Myristate | 5 |

-continued

Formulation 25:

| Components | % w/w |
|---|---|
| Hydroxypropyl Cellulose | 2 |
| Isopropyl Alcohol | 43 |
| Water | 20 |

Formulation 26:

| Components | % w/w |
|---|---|
| S-Ibuprofen | 5 |
| Propylene Glycol | 20 |
| Isopropyl Myristate | 5 |
| Hydroxypropyl Cellulose | 2 |
| Isopropyl Alcohol | 48 |
| Water | 20 |

Formulation 27 (placebo):

| Components | % w/w |
|---|---|
| (R/S)-Ibuprofen | 0 |
| Propylene Glycol | 21 |
| Isopropyl Myristate | 5.3 |
| Hydroxypropyl Cellulose | 2 |
| Isopropyl Alcohol | 50.8 |
| Water | 21 |

Formulation 27 was used as a vehicle formulation as a negative control (potential vehicle effects).

Experimental Procedure

MTT Direct Reduction Test

The endpoint of the EpiSkin® assay for skin irritation is the estimation of cell viability by assaying the reduction of methylthiazoldiphenyl-tetrazolium bromide (MTT) to its formazan metabolite by mitochondrial reductase. Some chemicals possess an intrinsic ability to perform this reduction. This can adversely affect the assay results, since MTT may be converted to formazan in the absence of metabolically viable cells. Therefore, before performing the EpiSkin® irritation assay, it was necessary to determine if the test items are capable of reducing MTT to formazan.

Direct reduction of MTT by the test item was assessed by adding the formulations and control (10 μL), to MTT solution in phosphate buffered saline (2 mL, 0.3 mg/mL MTT). The positive control was eugenol. The negative control was water. The formation of purple colored formazan was visually assessed after incubating for 3 h±5 min in a humidified incubator at 37° C. and a $CO_2$ level of 5%. Three replicate samples were assessed for each formulation. None of the tested formulations reduced MTT to formazan.

EpiSkin® Irritation Assay

The assay was carried out according to the performance standards specified by OECD:

OECD (2010), In Vitro Skin Irritation: Reconstructed Human Epidermis Test Method, OECD Guidelines for the Testing of Chemicals No. 439, OECD, Paris.

Test System Set Up

EpiSkin® units were shipped on transport agar in sterile plates of 12 individual units. Upon delivery, the condition of the EpiSkin® was assessed by checking the pH and temperature indicators. EpiSkin® units were transferred to 12 well plates containing EpiSkin® maintenance medium (2 mL). The tissues were then be incubated for 2 to 24 h in a humidified incubator at 37° C. and a $CO_2$ level of 5% before proceeding with exposure to the test formulations and control substances. The negative control was Dulbecco's phosphate buffered saline (PBS) and the positive control was an aqueous solution of sodium dodecyl sulphate (SDS, 5%, w/v).

The formulations were applied to the skin "without dilution". An aliquot (10 μL) of the undiluted formulations and control substances were applied to three replicate EpiSkin® tissues using a positive displacement pipette. The formulations and controls were gently spread over the entire surface of the exposed skin using the applicator tip.

The EpiSkin® was exposed to the formulations and control substances for 15 min±30 s. The EpiSkin® surface was then rinsed with PBS (ca 25 mL) and returned to a well containing fresh Maintenance Medium (2 mL). The treated EpiSkin® units were then incubated for 42 h±1 h in a humidified incubator at 37° C. and a $CO_2$ level of 5%.

MTT Assay

After the recovery period, EpiSkin® units were tapped dry and transferred to wells containing a solution of MTT in EpiSkin Assay Medium (2 mL, 0.3 mg/mL). The tissues were then incubated for 3 h±5 min in a humidified incubator at 37° C. and a $CO_2$ level of 5%. At the end of the incubation, EpiSkin® units were patted dry on absorbent paper and the central part of the membrane was collected with a biopsy punch. The upper cellular layer of the biopsy was separated from the underlying collagen matrix using forceps and both pieces placed into labeled microcentrifuge tubes. Formazan was extracted from the EpiSkin® by incubating each biopsy in acidified isopropanol (500 μL) for 68 h in a fridge at 4° C., protected from light. The cell viability of each tissue was calculated from optical density absorption readings with reference to the negative controls, which were assigned the nominal value of 100% viability.

Calculation of Cell Viability From MTT Assay Optical Density (OD) Readings

Optical Density ($OD_{550nm}$) readings were transferred into Microsoft Excel to allow further calculations to be performed.

Standard statistical techniques were used to calculate $OD_{blank\ mean}$: the average OD of the blank (acidified isopropanol containing) wells. The corrected OD for each sample or control was calculated by subtracting the value of $OD_{blank\ mean}$ from each reading:

$$OD_{corrected} = OD_{raw} - OD_{blank\ mean}$$

The % Viability for each sample and positive control was calculated as follows:

$$\%\ Viability = (OD_{corrected}/\text{mean}\ OD_{negative\ controls}) \times 100$$

Standard statistical techniques were used to calculate the mean viability (with standard deviation) for each test formulation, placebo (vehicle), and positive control. Formulations are considered to be irritant to skin in accordance with GHS category 2 if the tissue viability after exposure and post-treatment incubation is less than or equal (S) to 50%.

Table 8 shows the results of % Viability for Formulations 25-27.

TABLE 8

Percentage Viability of EpiSkin Cultures

| Treatment | Replicate ID | Relative Viability (%) | Mean Relative Viability per Tissue (%) | Mean Relative Viability per Treatment (%) | SD (%) |
|---|---|---|---|---|---|
| PBS Solution (Negative Control) | Rep 1 | 104.40<br>104.10 | 104.25 | 100.00 | 10.00 |
| | Rep 2 | 107.12<br>107.22 | 107.17 | | |
| | Rep 3 | 88.58<br>88.58 | 88.58 | | |
| Aqueous SDS Solution (5%, w/v) (Positive Control) | Rep 1 | 19.05<br>18.95 | 19.00 | 23.36 | 11.71 |
| | Rep 2 | 36.18<br>37.08 | 36.63 | | |
| | Rep 3 | 13.81<br>15.12 | 14.46 | | |
| Formulation 25 (S-Ibuprofen 10%, (w/w)) | Rep 1 | 89.79<br>91.20 | 90.49 | 88.95 | 5.41 |
| | Rep 2 | 93.32<br>93.52 | 93.42 | | |
| | Rep 3 | 82.33<br>83.54 | 82.94 | | |
| Formulation 26 (S-Ibuprofen 5%, (w/w)) | Rep 1 | 93.72<br>95.13 | 94.42 | 93.65 | 1.75 |
| | Rep 2 | 90.70<br>92.61 | 91.65 | | |
| | Rep 3 | 93.52<br>96.24 | 94.88 | | |
| Formulation 27 (Placebo) | Rep 1 | 98.35<br>97.75 | 98.05 | 98.69 | 2.38 |
| | Rep 2 | 96.64<br>96.74 | 96.69 | | |
| | Rep 3 | 101.68<br>100.97 | 101.33 | | |

While the invention has been described and pointed out in detail with reference to operative embodiments thereof, it will be understood by those skilled in the art that various changes, modifications, substitutions, and omissions can be made without departing from the spirit of the invention. It is intended therefore, that the invention embrace those equivalents within the scope of the claims that follow.

What is claimed is:

1. A composition for transdermal administration of ibuprofen or a salt thereof comprising, ibuprofen in an amount of about 5% by weight of the composition;

a gelling agent in an amount of about 1% to about 5% by weight of the composition;

propylene glycol in an amount of about 15% to about 25% by weight of the composition;

a lower alkyl alcohol in an amount of about 35% to about 60% by weight of the composition, wherein the lower alkyl alcohol is isopropyl alcohol or a mixture of isopropyl alcohol and ethanol;

isopropyl myristate in an amount of between about 1% and about 5% by weight of the composition;

water in an amount of between about 15% and about 30% by weight of the composition;

and a base in an amount sufficient for the composition to have an apparent pH of about 7.0.

2. The composition of claim 1, wherein the ibuprofen is substantially pure S(+)-ibuprofen.

3. The composition of claim 2, further comprising ethylene glycol or 1,3-butylene glycol.

4. The composition of claim 2, further comprising glycerol.

5. A method of reducing pain or inflammation comprising: administering to a dermal surface of a subject in need of a reduction in pain or inflammation a composition comprising, ibuprofen in an amount of about 5% by weight of the composition;

a gelling agent in an amount of about 1% to about 5% by weight of the composition;

propylene glycol in an amount of about 15% to about 25% by weight of the composition;

a lower alkyl alcohol in an amount of about 35% to about 60% by weight of the composition, wherein the lower alkyl alcohol is isopropyl alcohol or a mixture of isopropyl alcohol and ethanol;

isopropyl myristate in an amount of between about 1% and about 5% by weight of the composition;

water in an amount of between about 15% and about 30% by weight of the composition;

and a base in an amount sufficient for the composition to have an apparent pH of about 7.0.

6. The method of claim 5, wherein the ibuprofen is substantially pure S(+)-ibuprofen.

7. The method of claim 6, wherein the composition further comprises ethylene glycol or 1,3-butylene glycol.

8. The method of claim 6, wherein the composition further comprises glycerol.

9. The method of claim 5, wherein the dermal surface is on a neck, back, arm, hand, foot, leg, or joint of the subject.

* * * * *